(12) United States Patent
Zhang et al.

(10) Patent No.: US 12,167,919 B2
(45) Date of Patent: Dec. 17, 2024

(54) SYSTEM AND METHOD FOR NON-INVASIVE, INTRACRANIAL BRAIN MOTION MONITORING

(71) Applicant: The General Hospital Corporation, Boston, MA (US)

(72) Inventors: Quan Zhang, Winchester, MA (US); Gary Strangman, Boxford, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 18/538,583

(22) Filed: Dec. 13, 2023

(65) Prior Publication Data

US 2024/0115187 A1 Apr. 11, 2024

Related U.S. Application Data

(62) Division of application No. 17/863,002, filed on Jul. 12, 2022, now Pat. No. 11,883,182, which is a division of application No. 16/710,095, filed on Dec. 11, 2019, now Pat. No. 11,412,976, which is a division of application No. 14/900,840, filed as application No. PCT/US2014/044056 on Jun. 25, 2014, now Pat. No. 10,537,275.

(60) Provisional application No. 61/889,273, filed on Oct. 10, 2013, provisional application No. 61/839,053, filed on Jun. 25, 2013.

(51) Int. Cl.
*A61B 5/00* (2006.01)
*A61B 5/1455* (2006.01)

(52) U.S. Cl.
CPC .......... *A61B 5/4064* (2013.01); *A61B 5/0075* (2013.01); *A61B 5/14553* (2013.01); *A61B 5/6814* (2013.01)

(58) Field of Classification Search
CPC . A61B 5/4064; A61B 5/0075; A61B 5/14553; A61B 5/6814
See application file for complete search history.

(56) References Cited

U.S. PATENT DOCUMENTS

2002/0095087 A1* 7/2002 Mourad ............... A61B 8/0816
600/442

* cited by examiner

*Primary Examiner* — Joel F Brutus
(74) *Attorney, Agent, or Firm* — Quarles & Brady LLP

(57) ABSTRACT

A system and a method is provided for assessing motion of a biological tissue of a subject including one or more superficial biological layers and a targeted biological layer. A perturbation unit provide an optical perturbation to the one or more superficial biological layers. An optical signal generator transmits optical signals at one or more near-infrared wavelengths. An optical signal receiver acquires a set of optical signal data preceding, during, or following the optical perturbation at a first acquisition time relative to the optical perturbation. A signal processor determines, using the set of optical signal data, a set of optical characteristics and separates, using the set of optical characteristics, a target optical signal. The signal processor generates a report indicative of a movement of the targeted biological tissue within the subject. The movement of the targeted biological layer is calculated using the target optical signal.

20 Claims, 12 Drawing Sheets

SYSTEM AND METHOD FOR NON-INVASIVE, INTRACRANIAL BRAIN MOTION MONITORING

CROSS-REFERENCE TO RELATED APPLICATIONS

This application is a divisional of U.S. application Ser. No. 17/863,002, which is a divisional of U.S. application Ser. No. 14/900,840 filed on Dec. 22, 2015, which is a U.S. national stage application of PCT/US2014/044056 filed on Jun. 25, 2014, which claims the benefit of U.S. Provisional Patent Application No. 61/839,053, filed on Jun. 25, 2013, and U.S. Provisional Patent Application No. 61/889,273, filed on Oct. 10, 2013, the entire disclosures of which are incorporated herein by reference.

STATEMENT REGARDING FEDERALLY SPONSORED RESEARCH

This invention was made with government support under W81XWH1020199 awarded by the Department of Defense and SMST2801 awarded by the National Space Biomedical Research Institute. The government has certain rights in the invention.

BACKGROUND OF THE INVENTION

The invention relates generally to electro-optical methods and systems. More particularly, the invention relates to methods and systems directed to non-invasive monitoring of biologic tissues and motion thereof.

Despite the fact that approximately 1.7 million people are affected each year by traumatic brain injury (TBI), TBI remains an inadequately understood medical problem. The majority of TBI cases, some 80-90%, are characterized as mild TBI (mTBI), or concussions, and often result in few symptoms or sequelae, with many related to sports and recreation. The detailed pathophysiological mechanisms underlying TBI are complex, and many aspects of the injury process remain obscure. However, it is clear that there is an initial mechanical shock which can induce cellular compression and rending. Subsequent (secondary) brain damage can then result from: {1) insufficient oxygen supply (ischemia, hypoxia), (2) blood in contact with neurons or glia (hemorrhage), (3) inflammatory responses, (4) excitotoxic responses (post-injury glutamate release) , (5) cytotoxic edema and, (6) hemodynamic dysregulation. All of these secondary insults evolve over periods ranging from minutes to hours to months or longer. The clinical course following TBI can also include the sudden and unpredictable appearance of edema or hemorrhage. Management of acute and subacute TBI focuses on identifying and preventing secondary sequelae, given that they are often preventable and associated with poor outcome.

One key variable in mTBI diagnosis and prognosis is knowing the nature and extent of the impact to the head. However, a notable technological gap exists in the ability to non-invasively monitor the movement of the brain during head motion in vivo, including mechanical shock that induces the TBI. Commercial devices implementing accelerometry measurements have traditionally been used to help quantify hits to the head in sports like football or hockey or cycling. However, such information may only be used to infer how the brain moves inside the skull during sudden acceleration or deceleration of the head. Other approaches have generally been limited to animal models with invasive sensors, which inherently change the nature of the cranial cavity and hence can affect the measurement of brain motion or injury itself.

Consequently, considering such limitations of previous technological approaches, it would be desirable to have a system and method for non-invasively detecting and enhancing brain measurements resulting from acute injuries or medical conditions.

SUMMARY OF THE INVENTION

The present invention overcomes the aforementioned drawbacks by providing systems and methods for non-invasively detecting and enhancing brain measurements using near-infrared optical neuromonitoring, such as brain motion, mobility, activity, perfusion, oxygenation and so forth. Systems and methods in accordance with the present invention provide accurate models for head injuries and their consequences, including the ability to provide real-time monitoring during a mechanical impact by quantifying intracranial motion associated with multiple levels of acceleration and deceleration. In addition, the present systems and methods have the added advantages of being highly sensitive to cerebral blood volume and oxygenation in biological tissues, which are also important physiological variables in post-TBI brain assessment.

In accordance with the present invention, the method for assessing motion of a biological tissue of a subject, the biological tissue including one or more superficial biological layers and a targeted biological layer, includes arranging one or more wearable elements on the subject, the one or more wearable elements configured to transmit or receive optical signals at one or more near-infrared wavelengths. The method also includes acquiring a set of optical signal data using at least one of the one or more wearable elements preceding, during, or following an optical perturbation within the one or more superficial biological layers at a first acquisition time relative to the optical perturbation and determining, using the set of optical signal data, a set of optical characteristics representative of light transiting the one or more superficial biological layers and the targeted biological layer. The method further includes separating, using the set of optical characteristics and a model of the one or more superficial biological layers and the targeted biological layer, a target optical signal consistent with the targeted biological layer, wherein the model relates photon propagation through the one or more superficial biological layers and the targeted biological layer and optical properties of each superficial biological layer and the targeted biological layer. The method also includes generating a report indicative of the motion of the targeted biological layer within the subject, wherein the motion of the targeted biological layer is calculated using the target optical signal.

In accordance with the present invention, the system for assessing motion of a biological tissue of a subject, the biological tissue including one or more superficial biological layers and a targeted biological layer, includes one or more wearable elements configured to be arranged on the subject, the one or more wearable elements configured to allow transmission or reception of optical signals to and from the subject at one or more near-infrared wavelengths and one or more perturbation units to provide an optical perturbation to the one or more superficial biological layers. The system also includes an optical signal generator configured to transmit optical signals at the one or more near-infrared wavelengths via the one or more wearable elements, and an optical signal receiver configured to acquire a set of optical signal data from the wearable elements preceding, during, or following the compression at a first acquisition time relative to the optical perturbation. The system further includes a signal processor configured to determine, using the set of optical signal data, a set of optical characteristics representative of light transiting the one or more superficial biological layers and the targeted biological tissue. The signal processor is also configured to separate, using the set of optical characteristics and a model of the one or more superficial biological layers and the targeted biological layer, a target optical signal consistent with the targeted biological layer. Furthermore, the signal process is configured to generate a report indicative of a movement of the targeted biological tissue within the subject, wherein the movement of the targeted biological layer is calculated using the target optical signal.

In accordance with the present invention, the method for reducing interference in measurement of a biological tissue of a subject, the biological tissue including one or more biological layers and a targeted biological tissue, includes arranging one or more wearable elements on the subject, the one or more wearable elements configured to transmit or receive optical signals at one or more near-infrared wavelengths. The method also includes acquiring a set of optical signal data using at least one of the one or more wearable elements preceding, during, or following an optical perturbation within the one or more superficial biological layers at a first acquisition time relative to the optical perturbation and determining, using the set of optical signal data, a set of optical characteristics representative of light transiting the one or more superficial biological layers and the targeted biological layer. The method further includes separating, using the set of optical characteristics and a model of the one or more superficial biological layers and the target biological layer, a target optical signal consistent with the targeted biological layer from an interference signal consistent with the one or more superficial biological layers, wherein the model relates photon propagation through the one or more superficial biological layers and the targeted biological layer and optical properties of each superficial biological layer and the targeted biological layer, and generating a report indicative of a property of the targeted biological layer within the subject, wherein the property of the targeted biological layer is calculated using the target optical signal.

In accordance with the present invention, the system for reducing interference in measurement of a biological tissue of a subject, the biological tissue including one or more superficial biological layers and a targeted biological layer, includes one or more wearable elements configured to be arranged on the subject, the one or more wearable elements configured to allow transmission or reception of optical signals to and from the subject at one or more near-infrared wavelengths, and one or more perturbation units to provide an optical perturbation to the one or more superficial biological layers. The system also includes an optical signal generator configured to transmit optical signals at the one or more near-infrared wavelengths via the one or more wearable elements and an optical signal receiver configured to acquire a set of optical signal data from the one or more wearable elements preceding, during, or following the optical perturbation at a first acquisition time relative to the optical perturbation. The system further includes a signal processor configured to determine, using the set of optical signal data, a set of optical characteristics representative of light transiting the one or more superficial biological layers and the targeted biological tissue. The signal processor is also configured to separate, using the set of optical characteristics and a model of the one or more superficial biological layers and the targeted biological layer, a target optical signal consistent with the targeted biological layer from an interference optical signal consistent with the one or more superficial biological layers, wherein the model relates photon propagation through the one or more superficial biological layers and the targeted biological layer and optical properties of each superficial biological layer and the targeted biological layer. Furthermore, the signal processor is configured to generate a report indicative of a property of the targeted biological layer within the subject, wherein the property of the targeted biological layer is calculated using the target optical signal.

In accordance with the present invention, the method of reducing interference in optical spectroscopy of a biological tissue having one or more superficial biological layers and a targeted biological layer includes introducing a localized perturbation to at least one of the one or more superficial biological layers, transmitting an optical signal that interacts with the one or more superficial biological layers and the targeted biological layer, and receiving the optical signal. The localized perturbation is not introduced to the targeted biological layer.

In accordance with the present invention, the system for optical spectroscopy of a biological tissue having one or more superficial biological layers and a targeted biological layer includes one or more optical sources, one or more optical detectors, and one or more perturbation units for introducing an optical perturbation to the one or more superficial biological layers. The optical perturbation is not introduced to the targeted biological layer. At least one of the one or more optical sources is configured to transmit optical signals to interact with the one or more superficial biological layers and the targeted biological layer.

In accordance with the present invention, the method for assessing motion of a brain within a head of a subject includes arranging one or more wearable elements on the head of the subject, the one or more wearable elements configured to transmit or receive optical signals to or from the head of the subject at one or more near-infrared wavelengths and acquiring a set of optical signal data using at least one of the one or more wearable elements. The method also includes separating, using the optical signal data, a target optical signal consistent with the brain. The method further includes generating a report indicative of a movement of the brain within the head of the subject, wherein the movement of the brain is calculated using the target optical signal.

In accordance with the present invention, the system for assessing motion of a brain within a head of a subject includes one or more wearable elements configured to be arranged on the head of the subject, the one or more wearable elements configured to transmit or receive electromagnetic signals to and from the head of the subject at one or more near-infrared wavelengths. The system also includes an optical signal generator configured to transmit optical signals at the one or more near-infrared wavelengths via the one or more wearable elements and an optical signal receiver configured to acquire a set of optical signal data from the one or more wearable elements. The system further includes a signal processor configured to separate, using the optical signal data, a target optical signal consistent with the brain, and generate a report indicative of a movement of the brain within the head of the subject, wherein the movement of the brain within the head of the subject is calculated using the target optical signal.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Near-infrared neuromonitoring (NIN) offers the ability to track acute changes in cerebral hemodynamics non-invasively, since human tissue is sufficiently transparent to near-infrared (NIR) wavelengths (650-950 nm), to enable monitoring of the brain. Advantageously, NIR wavelengths are non-ionizing and do not harm biological tissue at typical power densities in the range of 1-4 $mW/cm^2$, as compared to ambient near-infrared light level on a sunny day is about 50 $mW/cm^2$. By employing multiple colors of NIR light on a scalp and placing a detector a few centimeters away, the recorded light intensity may be used to measure concentrations of oxy-hemoglobin ($HbO_2$), deoxy-hemoglobin (HHb), and total-hemoglobin (HbT), which is proportional to blood volume when hematocrit remains constant.

As used herein, reference to a wavelength for an optical signal refers to a wavelength at maximum intensity, an average wavelength of the wavelengths at half-maximum intensity, or other suitable means of representing a wavelength of an optical signal that are known to a person having ordinary skill in the art. As used herein, reference to different wavelengths refers to wavelengths that can be distinguished by technology that is available now or that becomes available in the future.

NIN instruments are most sensitive to the outermost 1-2 cm of brain tissue. Although NIN provides some information about deep brain structures, NIN is especially sensitive to the brain-skull interface. NIN has previously demonstrated a high sensitivity to blood volume changes due to hemorrhage, blood oxygenation changes related to ischemia or hypoxia, as well as changes in brain function.

Figure 1:
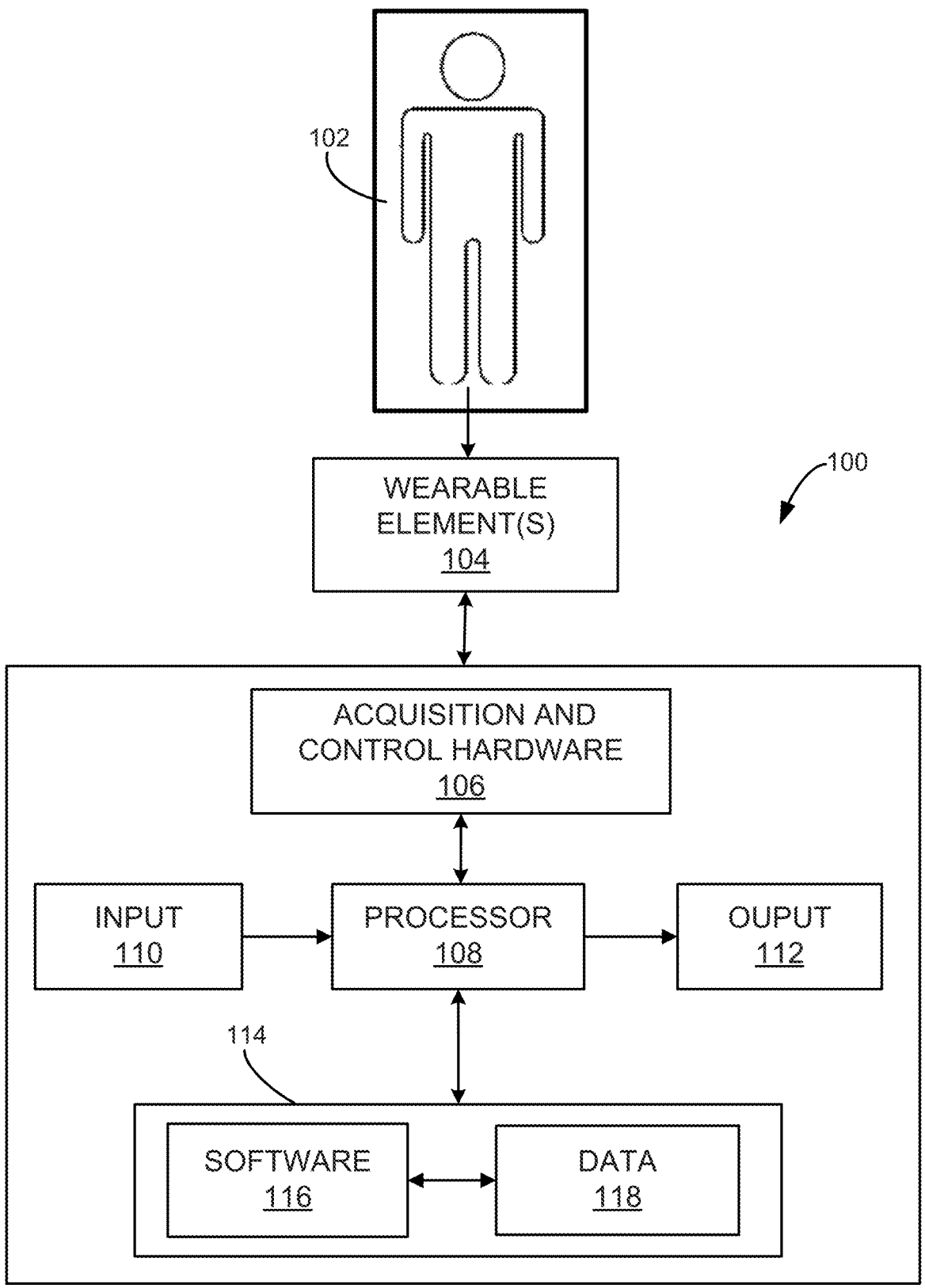
FIG. 1 is a schematic illustration of a system, in accordance with the present invention.

Turning to FIG. 1, a block diagram is shown of an exemplary system 100, which facilitates, among other things, the non-invasive detection of brain motion inside the skull of a subject 102. Thus, the system 100 may be a NIN system. The system 100 generally may include any number of wearable element(s) 104, acquisition and control hardware 106, a processor 108, an input 111, an output 112, a memory 114, and any other device for reading computer-readable media (not shown). The system 100 may be, for example, a wearable device, a workstation, a notebook computer, phone, a personal digital assistant (PDA), a multimedia device, a network server, a mainframe or any other general-purpose or application-specific computing device. The system 100 may operate autonomously or semi-autonomously, or in conjunction with other devices or hardware. The system 100 may also read executable software instructions from a computer-readable medium (such as a hard drive, a CD-ROM, flash memory and the like), or may receive instructions from a user, or any other source logically connected to computer or device, such as another networked computer or server. In one embodiment, the system 100 may be configured to acquire and analyze data for non-invasively assessing and monitoring intra-cranial injury. In another embodiment, the system 100 may be used to quantify brain motion associated with different types and levels of head or body movement. In yet another embodiment, the system 100 may be used to provide real-time monitoring of and feedback from a subject 102 engaged in any number of active or passive physical activities. In yet another embodiment, the system 100 may also monitor blood flow, or blood oxygenation or deoxygenation. In yet another embodiment, the system 100 may configured for usage on a head of a subject 102. In yet another embodiment, the acquisition and control hardware 106, the processor 108, the input 111, the output 112, the memory 114, or any other device for reading computer readable media (not shown) may be wearable by the subject 102.

The wearable element(s) 104 may be designed for receiving control and operation signals from the system 100 and for transmitting generated signal data along any number of channels. The wearable elements(s) 104 may be incorporated into or be part of items designed to be engaged with a subject 102 at any number of locations upon the subject 102, including for example on the head of a subject 102, in any number of geometrical configurations, and may be active or operational for any required or desired period of time. Communication between the wearable element(s) 104 and the system 100, or any other associated device or hardware, may be achieved by hard-wired connections or via remote or wireless means. In one embodiment, the wearable element (s) 104 may be configured to generate and detect multi-distance near-infrared spectroscopy optical signal data, accelerometry signal data, electrocardiography (ECG) signal data, blood flow data, blood oxygenation or deoxygenation data, and pressurization data, and any combination thereof. In another embodiment, any number of the wearable elements(s) 104 may be configured to generate, detect as well as affect, suppress or enhance signals from a subject 102, for example, by the application of electronic signals, mechanical forces, heating, and so on.

In one embodiment of the present invention, any number of the wearable element(s) 104 may be utilized in combination with separate systems, devices or units designed for variety of uses, such as delivering a compression using, for example, a headband. In another embodiment, any number of the wearable elements(s) 104 may integrate a combination of functionalities. In one such example, shown in FIG. 2A and FIG. 2B, the wearable element(s) 104 may include a near-infrared optical source or detector that may be combined with a pressure or compression delivery mechanism. In another such example, the wearable element(s) 104 may include a near-infrared optical source and detector. In yet another such example, the system 100 may include one or more perturbation units to provide an optical perturbation.

Figure 2A:
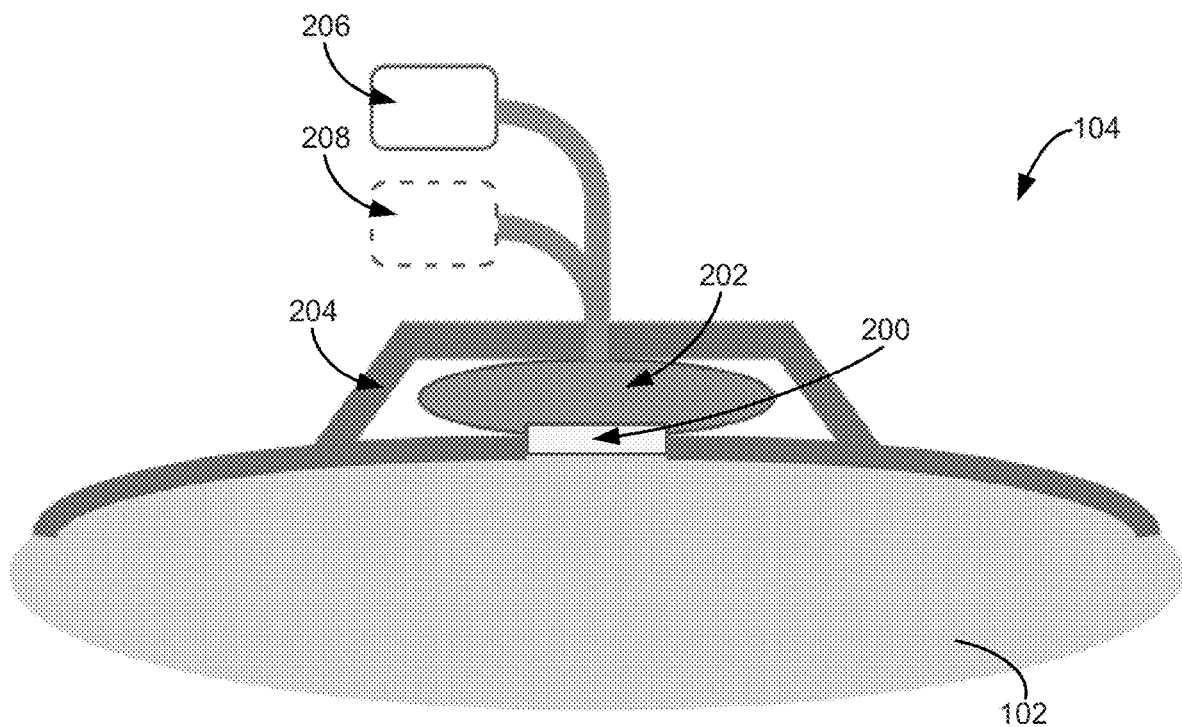
FIG. 2A is a schematic representative of a wearable element configured to apply a compression via an inflatable enclosure, in accordance with the present invention.

In FIG. 2A, the wearable element(s) 104 includes an optical component 200, which may be an near-infrared optical source or detector, an inflatable enclosure 202, which may be in the form of an airbag and the like, a support structure 204, a pumping station 206, and a pressure monitor unit 208 as needed. The support 204 may include any means necessary for fastening, securing or adhering any of the wearable element(s) 104 to a subject 102. The pressure of the enclosure 202 may be elevated, changed, or temporally modulated either autonomously or semi-autonomously, using the pumping station 206, as required or desired for compression of a tissue of the subject 102. In one aspect, an inflation, change or modulation may be performed to overcome an arterial blood pressure, either during operation of the optical component 200, or at any other time before or thereafter. In one aspect, an inflation, change or modulation may induce an optical perturbation in the subject 102. In certain embodiments, the inflation, change or modulation may induce an optical perturbation in one or more superficial biological layers, thereby allowing optical signals associated with the one or more superficial biological layers to be isolated from a target optical signal.

In certain embodiments, a set of optical signal data may be acquired preceding, during, or following an optical perturbation within one or more superficial biological layers. In certain embodiments, the set of optical signal data may be acquired at a first acquisition time relative to the optical perturbation. In certain embodiments, a set of unperturbed optical signal data may be acquired in the absence of the optical perturbation or preceding, during, or following the optical perturbation. In certain embodiments, the set of unperturbed optical signal data may be acquired preceding, during, or following the optical perturbation at a second acquisition time relative to the optical perturbation that is distinct from the first acquisition time. As used herein, a distinct time is a time that is measurably distinguishable from another time. It should be appreciated that an acquisition time relative to an optical perturbation can include a time before a start of a perturbation, a time after an end of a perturbation, a time after a start of a perturbation but before an end of a perturbation, a time at a start of a perturbation, or a time at an end of a perturbation. In certain embodiments, a set of optical signal data may be acquired during an optical perturbation within one or more superficial biological layers and a set of unperturbed optical signal data may be acquired in the absence of the optical perturbation. In certain embodiments, a set of optical characteristics representative of light transiting the one or more superficial biological layers and the targeted biological layer may be determined using the set of optical signal data and optionally the set of unperturbed optical signal data.

Figure 2B:
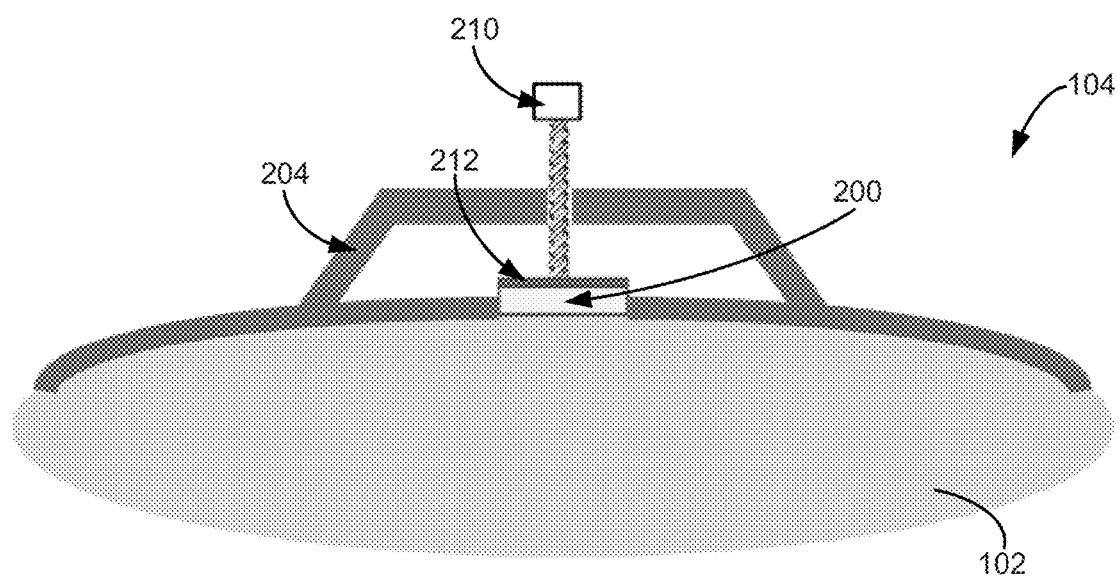
FIG. 2B is a schematic representative of a wearable element configured to apply a compression via an advancing element, in accordance with the present invention.

A variation on this design is shown in FIG. 2B, wherein a pressure or compression is mechanically applied using a compressive element 210, such as a screw, which may be advanced or translated towards or away from the tissue of a subject 102 either manually, or automatically via a motorized gear system (not shown). The level of compression may be monitored via a pressure sensor 212.

In certain embodiments, the optical perturbation may be induced in other ways, for example, by introducing a contrast agent or vasoactive substance into the one or more superficial biological layers that is not introduced into the targeted biological layers. As another example, the optical perturbation may be induced by inducing a localized temperature in the one or more superficial biological layers in order to induce an optical perturbation, for example, by causing blood vessel dilation or contraction in the one or more superficial biological layers, thereby changing the vascular blood content therein.

Returning to FIG. 1, the acquisition and control hardware 106 of the system 100 may be designed to produce, command, and control signals for the wearable elements(s) 104 so as to generate signal data continuously or intermittently, and relay the generated signal data for processing by processor 108. In one aspect, the acquisition and control hardware 106 may be configured for non-invasively assessing and monitoring intra-cranial injury, or for quantifying brain motion associated with different types and levels of acceleration and or deceleration, or for providing real-time monitoring of and feedback from a subject 102 engaged in any number of active or passive physical activities, by sending, receiving and processing near-infrared optical signals by processor 108. In another aspect, the acquisition and control hardware 106 may be configured for monitoring blood volume, blood flow, and/or blood oxygenation or deoxygenation, or respiration, and relay the generated data for processing by processor 108. In yet another aspect, the acquisition and control hardware 106 may be configured to direct and monitor an applied pressure, for example, achieved by any of the wearable element(s) 104 or any other pressurization unit or device integrated in a direct or indirect collaboration with the wearable elements(s) 104.

Operation of the acquisition and control hardware 106 for generating or acquiring signal data may require operator direction, input or feedback, or may be designed to operate autonomously, or be activated upon fulfillment of any set of pre-determined internal or external physical conditions or triggers. Signal data may be sampled at any acquisition rates, including for example, high sample rates. In one aspect, the sample rate may be 250 Hz. A person having ordinary skill in the art should appreciate that the sample rate should be high enough to provide a sufficient number of measurements to distinguish the signal that is being measured.

The processor 108 may be configured to process the generated signal data, including near-infrared spectroscopy optical signal data, ECG data, accelerometry data, blood oxygenation data, temperature data, respiration data, pressurization data and so forth. In one embodiment, the processor 108 may be designed to process optical signal data from one or more wearable elements 104 for the purpose of identifying or quantifying a movement of the desired biological tissue using the optical signal, the movement resulting from, for example, different types and levels of acceleration and/or deceleration of subject 102 engaged in any number of active or passive physical activities.

The input 110 may take any shape or form, as desired, for operation of the system 100, including the ability for selecting, entering, combining or otherwise specifying elements and/or parameters consistent with a specific set of measurements or monitoring configuration or scenario and the ability to initiate, program or select measurements related to specific timings of internal and external physical events. In one embodiment, the input 110 may be configured to accept functional and/or anatomical information of biological tissues that is not acquired by the one or more wearable elements 104, such as, for example, any type obtained from imaging data representing functional behavior and/or anatomical configurations, such as, for example, MRI data or ultrasound imaging data.

It should be appreciated that the processor 108 may receive and process additional data from other devices or sensors (not shown) beside the wearable element(s) 104 of the system 100 or from other devices or sensors that are coupled to the system 100. In certain embodiments, this additional data may be received at the acquisition and control hardware 106 or the input 110.

The output 112 may take any shape or form, as desired, and may include a visual and/or audio system, configured for indicating or reporting, for example, the time variation of measured and processed hemodynamic signals resulting from near-infrared photons traversing different biological tissues along a variety of paths.

The memory 114 may contain software 116 and data 118, and may be configured for storage and retrieval of information and data to be processed by the processor 108. In one aspect of the invention, the software 116 may contain instructions directed to performing simulations or modeling of near-infrared photon propagation in layered tissues.

Figure 3:
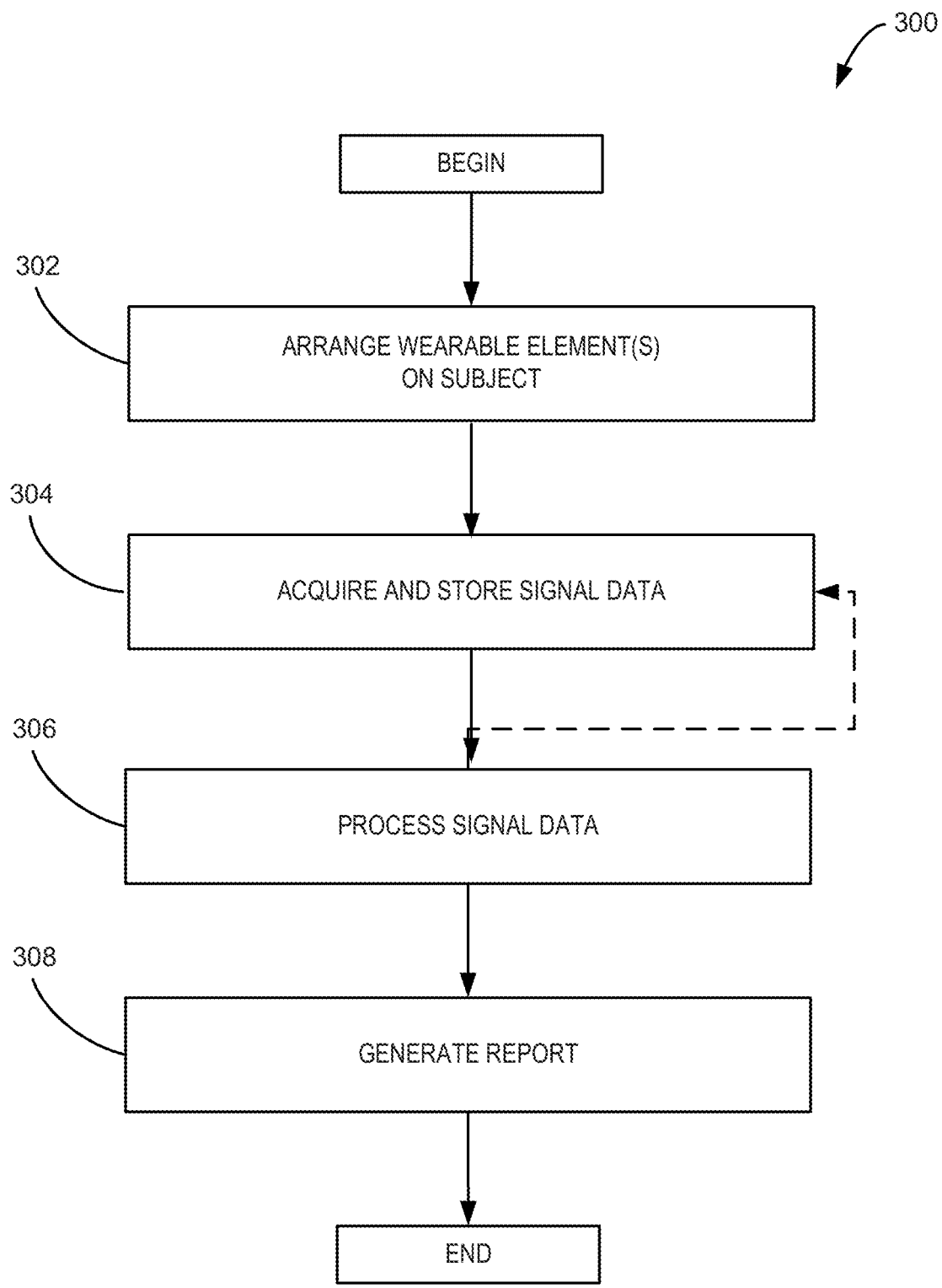
FIG. 3 is a flowchart setting forth the steps of a method for operating a system, in accordance with the present invention.

Usage of the system 100 is illustrated by the process 300 flowchart shown in FIG. 3. The process 300 begins at process block 302 whereby any number of desired wearable element(s) 104 are arranged at a variety of locations upon a subject 102, such as the head of a subject 102, as necessary or desired. At process block 304, any amount of required or desired signal data (i.e., a set of optical signal data, ECG data, EEG data, or accelerometry data) may be acquired from the wearable element(s) 104 and may be collected, stored or otherwise monitored for any specified or desired period of time. In certain embodiments, the set of optical signal data may comprise raw optical data (i.e., data as it was acquired or data with minimal manipulation). Activation of process block 304 may take place upon instruction or indication from an operator, or may automatically executed upon fulfillment of any set of pre-determined internal or external physical conditions or triggers. The acquired signal data from process block 304 may be stored partially or in its entirety in memory 114 and may be subsequently retrieved for processing or output. The signal data may then be processed at process block 306. At this point, additional signal data may then be acquired or monitored by returning to and repeating process block 304.

For a NIN measurement, a sensitivity may be defined as the change in an optical signal (or response) caused by a unit perturbation in target tissue optical property (or contrast). The response is usually expressed in optical density (OD) units, where :

$$\delta OD = \log \frac{\phi_0}{\phi}; \quad (1)$$

where $\phi_0$ is the baseline signal intensity and $\phi$ is the perturbed signal intensity. During functional brain activation, a major contrast is due to changes in tissue absorption caused by altered brain hemodynamics (blood volume and oxygenation).

For a non-invasive NIN measurement on, for example, the head of a subject 102, the total signal intensity measured at the scalp surface is related to the mean distance, or path length, that photons travel from a source to a detector. The total path length can be divided into a set of partial path lengths, each representing the distance that a given photon travels through any specific tissue type. The partial path length is related to an optical signal change according to:

$$\frac{\log \frac{\phi_0}{\phi}}{\delta \mu_{a\_j}} = PPL_k. \quad (2)$$

Since the sensitivity is defined as the change in signal ($\delta OD$) per unit change in optical properties, ($\delta \mu_{a\_j}$), the absolute sensitivity of a measurement to a given tissue type is then the mean path length traveled through that tissue type, j.

In general, for a multi-layer medium $\delta OD_i$ measured at a source-detector separation $SD_i$ is the sum of consequences of the absorption change at each layer:

$$\delta OD_i = \sum_{j=1}^{k} PPL_j^i \delta \mu_{a\_j}. \quad (3)$$

Here $PPL_j^i$ is the partial path length for measurement i in layer j. In other words, it is the sensitivity of measurement i ($\delta OD_i$) to optical absorption changes in layer j ($\delta \mu_{a\_j}$). Here $\delta OD_i$ is measurement I, $\delta \mu_{a\_j}$ is the optical absorption change in layer j. The major problem using Eqn. 3 is that the sensitivities $PPL_j^i$ are unknown. They can be estimated using Monte Carlo simulations, and cannot be measured experimentally; therefore in the past Eqn. 3 is mostly of theoretical value.

However, in accordance with the present invention, it was recognized that experimental measurements, for example using a multi-distance probe or an optical perturbation, can be combined with Eqn. 3 to remove superficial layer interference in the measurement of brain activity. As such, signal processing can be performed to isolate signals specific to a targeted tissue or organ within the subject, such as the brain. Referring again to FIG. 3, once the requisite or desired amount of signal data has been generated and processed by repeating process blocks 304 and 306, a report may be generated at process block 308. As will be described, the report may take any shape or form. In one aspect, the report may include an audio or visual indicator providing instruction or direction to the subject 102. In another aspect, the report may be a real-time readout or other real-time signal (e.g., alarm).

Below is an example illustrating this approach using a 2 distance probe and simplified 2 layer model of the head. In the following, a basic model of the head can be used that assumes the head to contain two layers: superficial layer (layer 1) and brain layer or target layer (layer 2). Collecting noninvasive optical signal data on the head using two source-detector distance probe, namely distance A (near) and B (far), then the following equations may be written:

$$\delta OD_A = PPL_1^A \delta \mu_{a\_1} + PPL_2^A \delta \mu_{a\_2} \quad (4);$$

$$\delta OD_B = PPL_1^B \delta \mu_{a\_1} + PPL_2^B \delta \mu_{a\_2} \quad (5).$$

If distance A is very short, then the sensitivity of SOD A to the brain layer (layer 2) optical absorption changes is very small and can be ignored; that is, $PPL_2^A=0$. Therefore, Eqn. 4 can be written as:

$$\delta OD_B = PPL_1^B \delta\mu_{a\_1} \quad (6).$$

If an optical perturbation is introduced to the superficial layer (layer 1) only, for example, by compressing the superficial temporal arteries, then $\delta\mu_{a\_2}=0$, and Eqn. 5 can be written as:

$$\delta OD_B = PPL_1^B \delta\mu_{a\_1} \quad (7).$$

A ratio k using Eqn. 6 and Eqn. 7 may then be defined as follows:

$$\frac{\delta OD_A}{\delta OD_B} = \frac{PPL_1^A \delta\mu_{a\_1}}{PPL_1^B \delta\mu_{a\_1}} = \frac{PPL_1^A}{PPL_1^B} = \frac{1}{k}. \quad (8)$$

In other words, the ratio of $$\frac{PPL_1^A}{PPL_1^B}$$

can now be represented as 1/k, or $$\frac{\delta OD_A}{\delta OD_B},$$

a value which can be experimentally measured.

Once k is acquired, for general measurements where optical property changes happen in both layers 1 and 2, Eqn. 5 can be written as:

$$\delta OD_B = PPL_1^B \delta\mu_{a\_1} + PPL_2^B \delta\mu_{a\_2} = kPPL_1^A \delta\mu_{a\_1} + PPL_2^B \delta\mu_{a\_2} = k\delta OD_A + PPL_2^B \delta\mu_{a\_2} \quad (10);$$

or $$PPL_2^B \delta\mu_{a\_2} = \delta OD_B - k\delta OD_A \quad (11).$$

Intuitively, equation (11) implies that the superficial layer interference $PPL_1^B \delta\mu_{a\_1}$ can now be experimentally estimated by using the short distance measurement $\delta OD_A$ and the coefficient k, in order to be removed from the far distance measurement $\delta OD_B$.

The 2-layer example described above illustrates an approach to manipulate signals stemming from superficial layers to enhance or clarify signals from deeper layers. In general, any signals originating from any number of layers, located either superficially or at any depth in tissue, may be manipulated as preferred or required to enhance or clarify signals from any desired layers. As such, any specific models may be devised according to equation 3 to account for the requisite or desired number of layers. For example, one such model may involve 3 layers, including scalp, skull and brain tissues without loss of generality.

In certain embodiments, the methods and systems are intended for use with a biological tissue of a subject, the biological tissue comprising one or more superficial biological layers and a targeted biological layer. In certain embodiments, the one or more superficial biological layers may comprise a scalp layer, a skull layer, or a combination thereof. In certain embodiments, the targeted biological layer may comprise a brain tissue layers and a targeted biological tissue layer. In certain embodiments, the one or more superficial biological tissue layers may comprise a scalp layer, a skull layer, or a combination thereof. In certain embodiments, the targeted biological tissue layer may comprise a brain tissue layer. As used herein, the term layer can be interpreted broadly to include any bulk material with a definable boundary. For example, a layer could take the form of a sheet, a block, a sphere, a disc, a column, or other three-dimensional shapes having reasonably discrete boundaries. The definable boundary may separate materials based on their composition or based on one or more properties of the materials.

Figure 4:
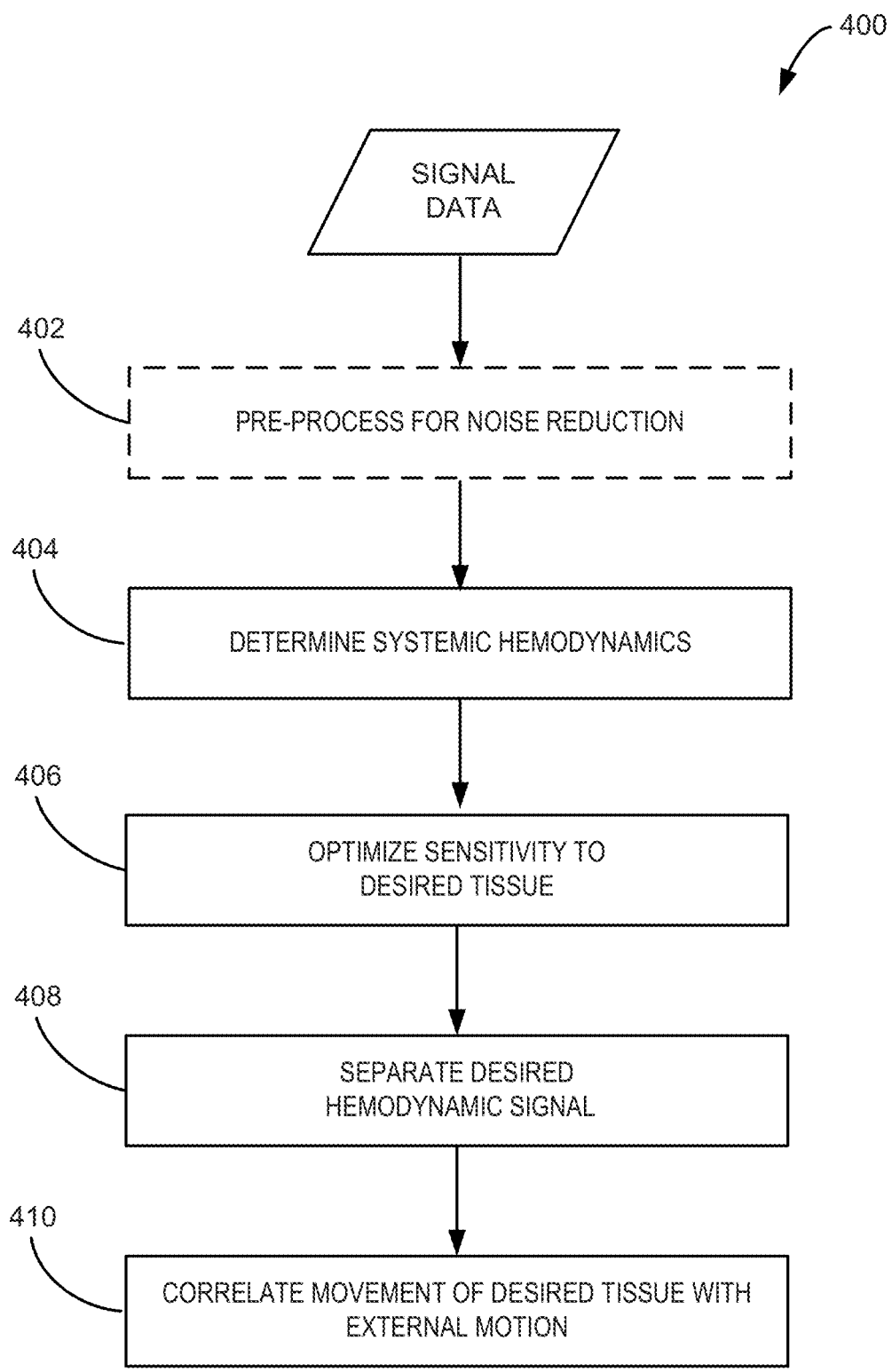
FIG. 4 is a flowchart setting forth the steps of identifying a brain movement in relation to external motion, in accordance with the present invention.

Turning now to FIG. 4, a flowchart illustrates the process 400 of determining and quantifying a brain movement using the approach described above. The process 400 may begin at process block 402 where the optical signal data undergoes any number of pre-processing steps to reduce or eliminate confounding noise signals, such as noise signals from cardiac activity, respiration, and spontaneous low frequency oscillations, among others. Noise reducing techniques applied at process block 402 may involve any combination of frequency-dependent or frequency-independent signal rejection, adaptive filtering algorithms techniques, and so forth. Next, at process block 404, systemic hemodynamics are determined based on the filtered signal data from process block 402. Next, at process block 406, the sensitivity to the hemodynamics of a desired biological tissue or target biological layer, such as the brain of a subject 102, is optimized. This step may be accomplished using the algorithm described above.

Figure 5:
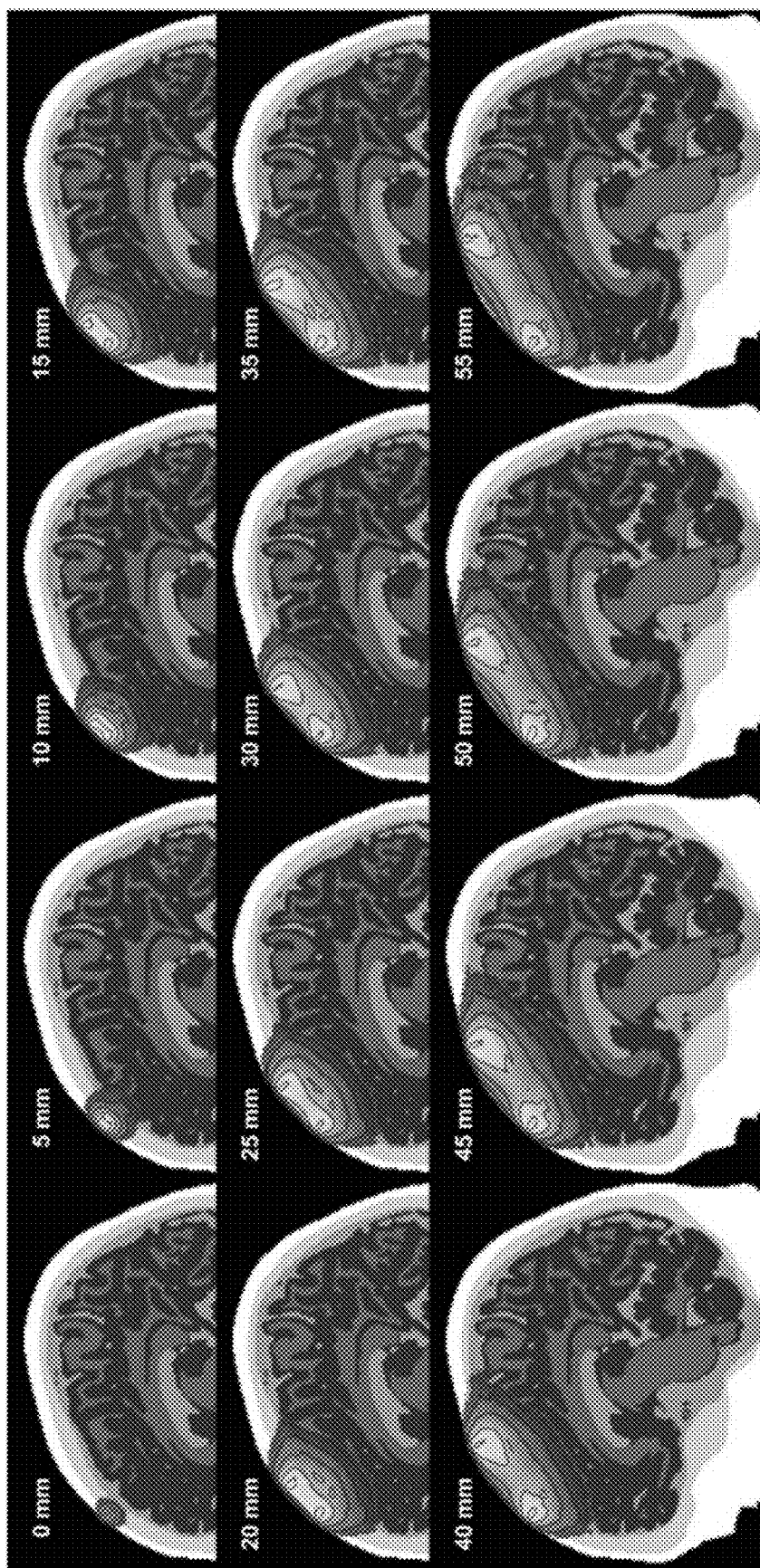
FIG. 5 is an illustration of photon sensitivity profiles for a broad range of optical source-detector separations, in accordance with the present invention.

In one aspect, a variable number of near-infrared optical source-detector distances may be utilized to obtain multiple signal sensitivities to different biological tissues, such as brain or scalp, such as shown in FIG. 5. In another aspect, a variable number of near-infrared wavelengths may be utilized to obtain multiple signal sensitivities to different components of the biological tissues, such as oxy-hemoglobin and deoxy-hemoglobin.

In certain embodiments, the one or more wearable elements 104 may comprise a first source-detector distance and a second source-detector distance that is different than the first source-detector distance. In certain embodiments, the one or more wearable elements 104 may comprise a third, fourth, fifth, sixth, or nth distinct source-detector distances. In certain embodiments, the one or more wearable elements 104 may be configured to transmit and receive electromagnetic signals at a first near-infrared wavelength and a second near-infrared wavelength that is different than the first near-infrared wavelength.

In certain embodiments, the one or more wearable elements 104 may be configured to transmit and receive electromagnetic signals and a third, fourth, fifth, sixth, or nth distinct near-infrared wavelength. In certain embodiments, the first near-infrared wavelength may be relatively more sensitive to a first component of the biological tissue and the second near-infrared wavelength may be relatively more sensitive to a second component of the biological tissue. In certain embodiments, the first component may be oxy-hemoglobin and the second component may be deoxy-hemoglobin.

In certain embodiments, the one or more wearable elements 104 may comprise a first source-detector distance and a second source-detector distance that may be different than the first source-detector distance, wherein the one or more wearable elements 104 may be configured to transmit and receive electromagnetic signals at a first near-infrared wavelength over the first source-detector distance and electromagnetic signals at the first near-infrared wavelength over the second source-detector distance, and wherein the one or more wearable elements 104 may be configured to transmit and receive electromagnetic signals at a second near-infrared wavelength over the first source-detector distance and electromagnetic signals at the second near-infrared wavelength over the second source-detector distance, wherein the second near-infrared wavelength may be different than the first near-infrared wavelength.

In another aspect, optimizing the hemodynamic signals from a desired biological tissue involves providing a perturbation to a superficial layer only, such as a compression to the superficial temporal arteries of a scalp.

In certain embodiments, the methods may comprise determining, from a set of optical signal data and optionally a set of unperturbed optical signal data, a set of optical characteristics representative of light transiting one or more superficial biological layers and the targeted biological layer. In certain embodiments, the set of optical characteristics may include layer thicknesses, layer optical absorption coefficients, layer optical scattering characteristics, layer density characteristics, or other optical characteristics that a person having ordinary skill in the spectroscopic arts would recognize as useful for the measurements described herein.

Figure 6:
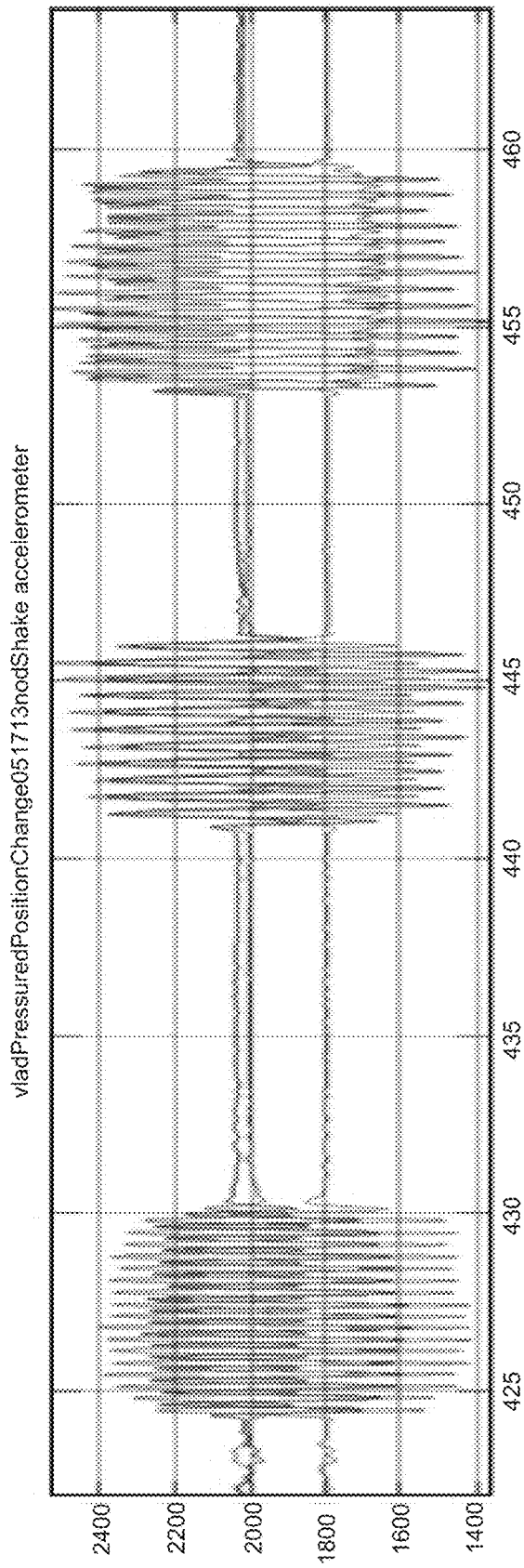
FIG. 6 is a graphic example illustrating a sensitivity to the motion of a brain inside the skull as a result of a compressive perturbation, in accordance with the present invention.
Figure 6:
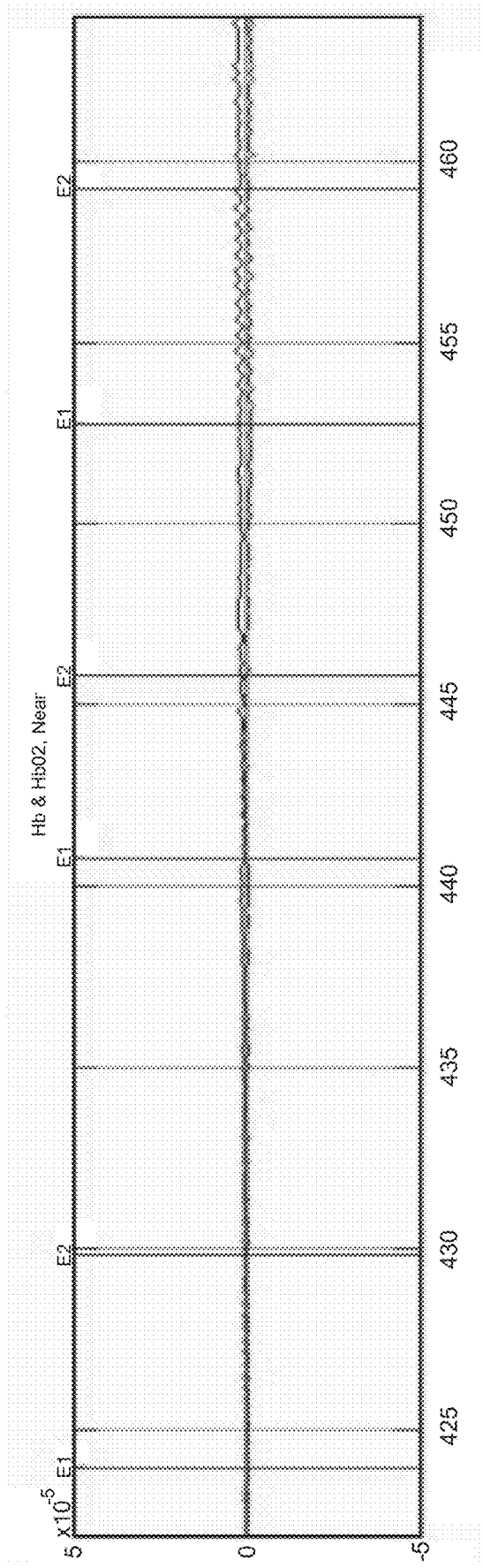
Figure 6:
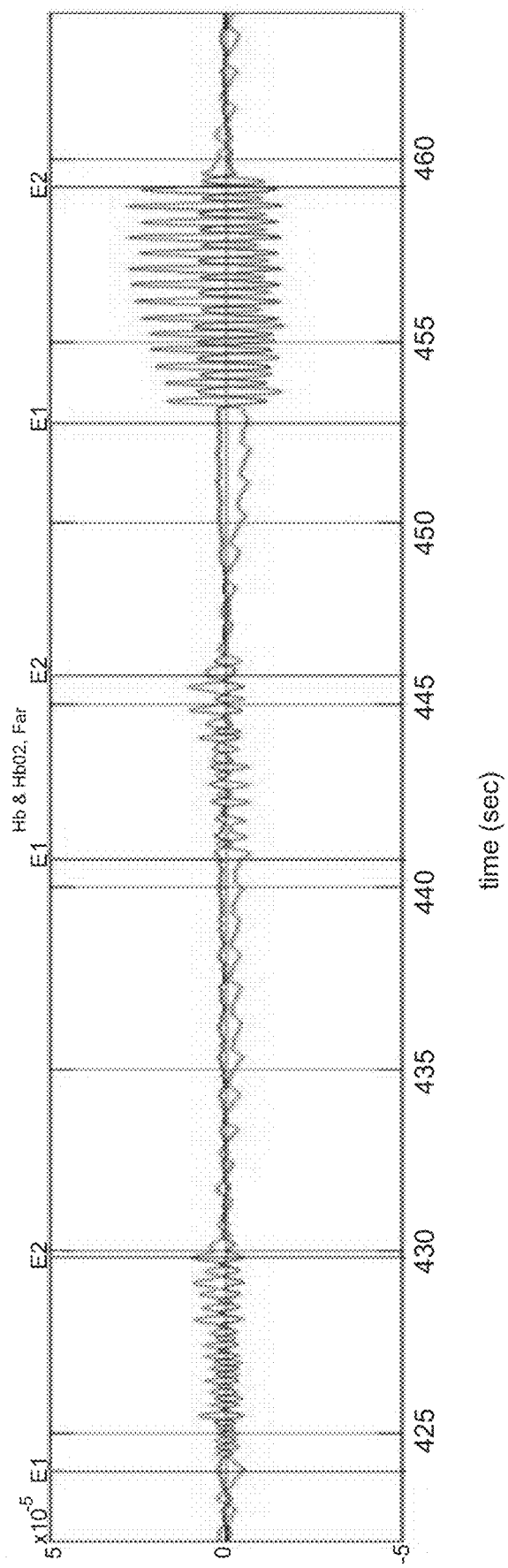

Providing a perturbation to a superficial layer alone is illustrated by an example in FIG. 6, where time varying monitoring of a moving head of a subject (top panel) is performed with a compression (i.e., an optical perturbation) applied to the superficial temporal arteries of the scalp at a pressure exceeding arterial blood pressure. The compression is shown to nearly eliminate signals from sensors configured to detect scalp only (middle panel), wherein the scalp signals would typically be larger than brain signals. The bottom panel shows sensors configured to detect brain and scalp signals. The absence of scalp signals in the middle panel combined with large oscillations in the bottom panel reveals a clear sensitivity specifically to brain tissue.

In certain embodiments, an optical perturbation may be induced by compressing one or more blood vessels associated with one or more superficial biological layers at a compression pressure that exceeds a pre-determined vascular pressure. In certain embodiments, the pre-determined vascular pressure may be between about 0.01 millimeters of mercury and about 1000 millimeters of mercury. In certain embodiments, the pre-determined vascular pressure may be between about 1 millimeter of mercury and about 500 millimeters of mercury. In an embodiment that is typical for human biology, the pre-determined vascular pressure may be between about 5 millimeters of mercury and about 200 millimeters of mercury. In certain embodiments, the pre-determined vascular pressure may be an arterial blood pressure of the subject. In certain embodiments, an optical perturbation may comprise a perturbation of a vascular pressure within one or more biological layers. In certain embodiments, the optical perturbation may be introduced to the one or more superficial biological layers, but may not be introduced to the targeted biological layer. It should be appreciated that, while the optical perturbation need not be modulated, a modulation of the optical perturbation may be paired with lock-in detection to further enhance and isolate a target signal consistent with the target biological layer from an interference signal consistent with one or more superficial biological layers.

Figure 7:
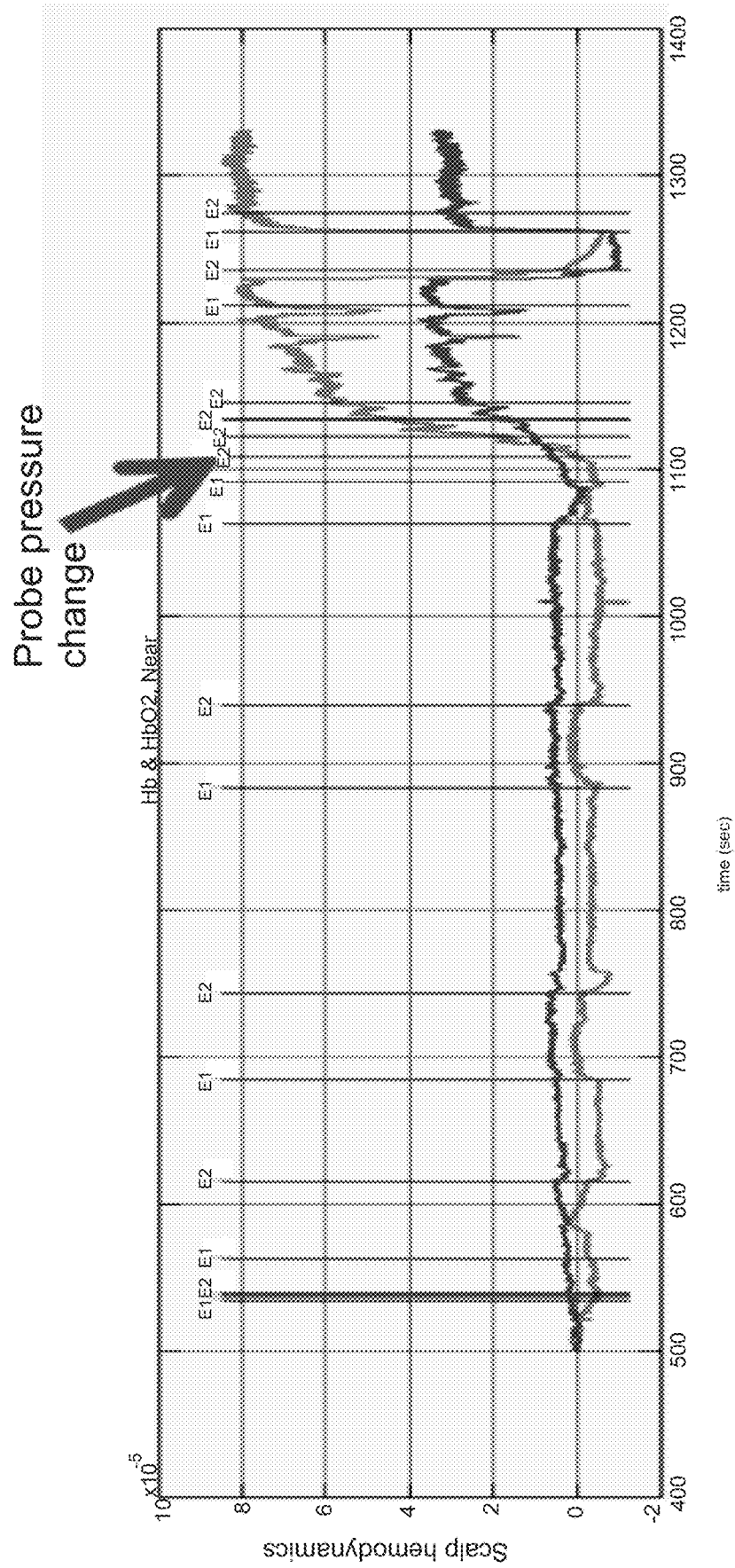
FIG. 7 is a graphic example illustrating the effects of change in compressive pressure on the hemodynamics of the brain with and without scalp-only hemodynamics correction, in accordance with the present invention.
Figure 7:
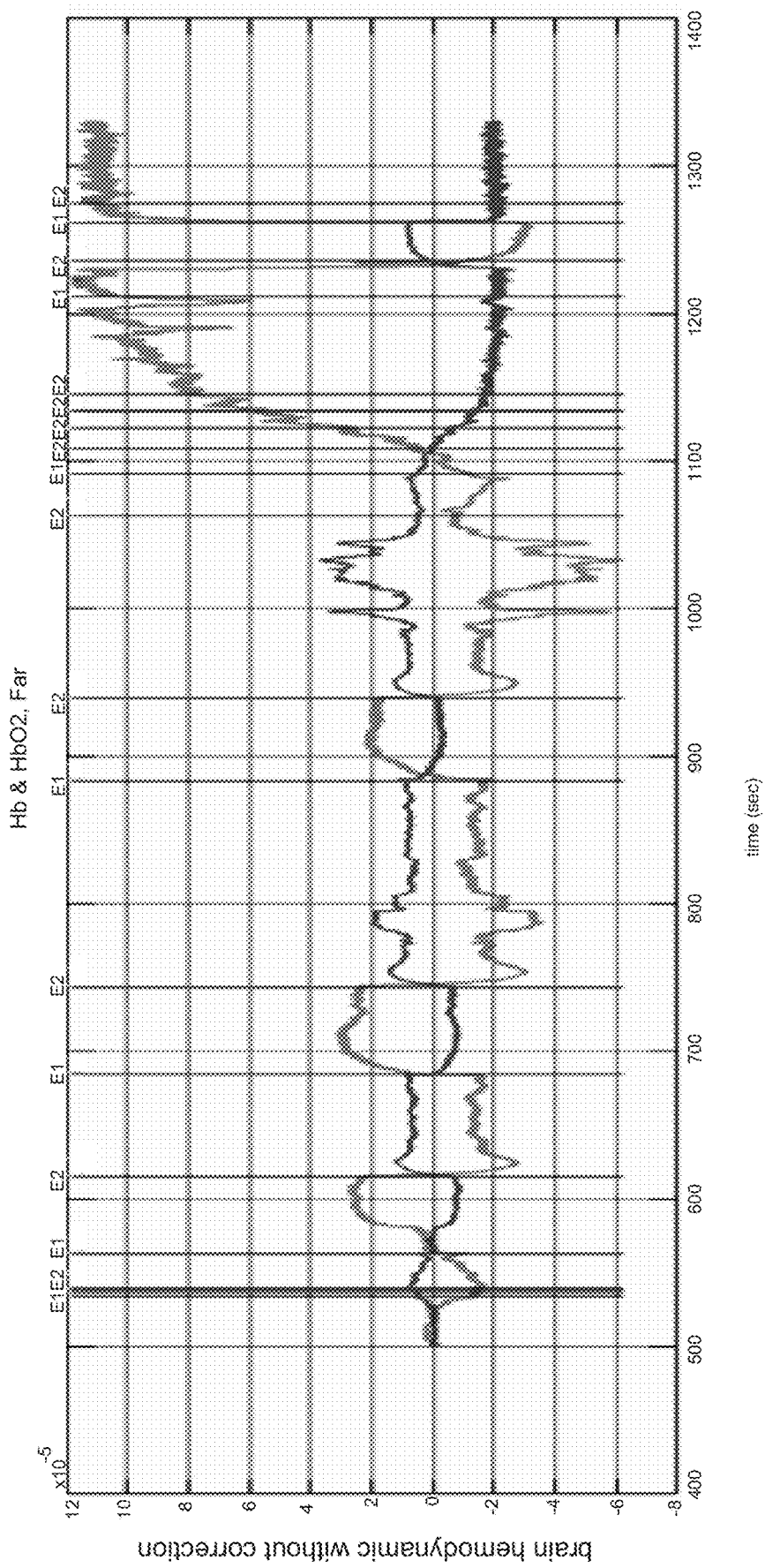
Figure 7:
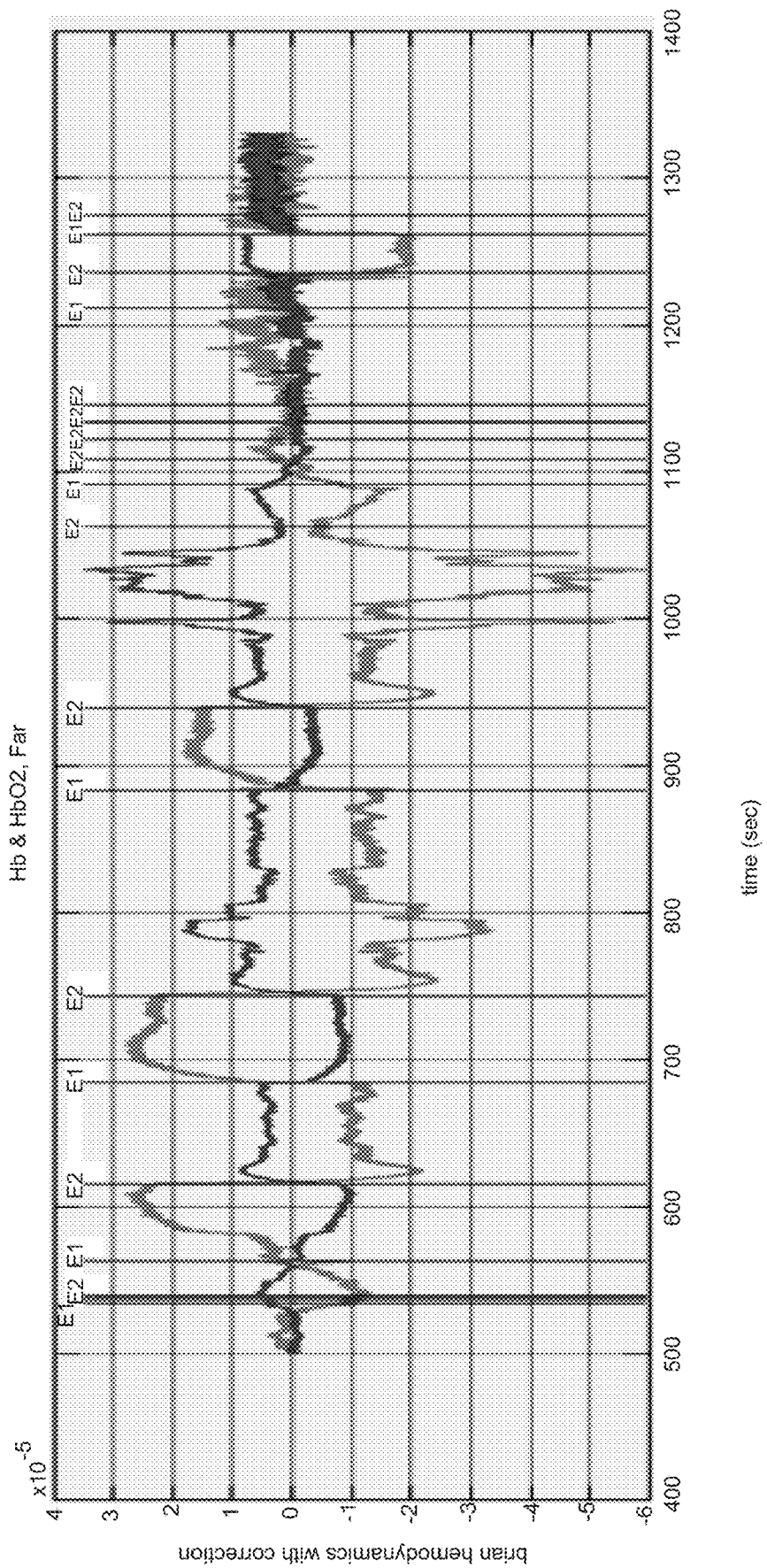

Another example, shown in FIG. 7, further illustrates the effects of compression upon hemodynamic signals. Sensors sensitive to scalp (top panel) and scalp plus brain (middle panel) recorded hemodynamic changes associated with head orientation (and presumed brain movement within the skull), seen as three rounded square-wave functions from 550-950 sec on the time axis collected during changes in body orientation. These were recorded with scalp compression. When the scalp compression was released (arrow), scalp hemodynamics and uncorrected brain hemodynamics changed dramatically. Using the compression-release signal along with a model of NIN signals, as described above, the large scalp-only hemodynamic change from the scalp plus brain measurement (namely, the release of scalp vessel compression at 1100 sec) is removed without reducing or otherwise affecting the signal associated with changes in head orientation (bottom panel).

Returning to FIG. 4, process block 408 uses the above-described approach to separate the hemodynamics of a desired tissue, such as those of the brain, from systemic hemodynamics. In this manner, the present invention provides a way of separating systemic hemodynamics from brain hemodynamics, which dramatically increases the signal-to-noise of NIRS to brain tissue in many settings. In one aspect, a model of the one or more superficial biological layers and the targeted biological layer may be utilized to separate a target optical signal consistent with the targeted biological layer and optionally an interference signal consistent with the one or more superficial biological layers. In certain embodiments, the model may relate photon propagation through the one or more superficial biological layers and the targeted biological layer and optical properties of each superficial biological layer and the targeted biological layer. Then, at process block 410, the separated hemodynamic signals (i.e., the target optical signal and the interference signal), combined with external motion information, such as head acceleration or deceleration, are used to determine the movement of a desired tissue with respect to external motion, such as the brain in relation to the skull. It should be appreciated that the output of process block 408 contains information relating to the movement of the target biological layer, which may be relative to the superficial biological layer, so in some embodiments, process block 410 may not be necessary.

In certain embodiments, the methods comprise generating a report (process block 308) indicative of a property of a targeted biological layer within the subject, wherein the property of the targeted biological layer may be calculated using the target optical signal. In certain embodiments, the property may be motion, oxygenation, perfusion, brain function, or combinations thereof. In certain embodiments, generating a report and calculating the property may be separate process steps (process block 308 and process block 410, respectively) or may be performed in a single process step (process block 308).

Figure 8:
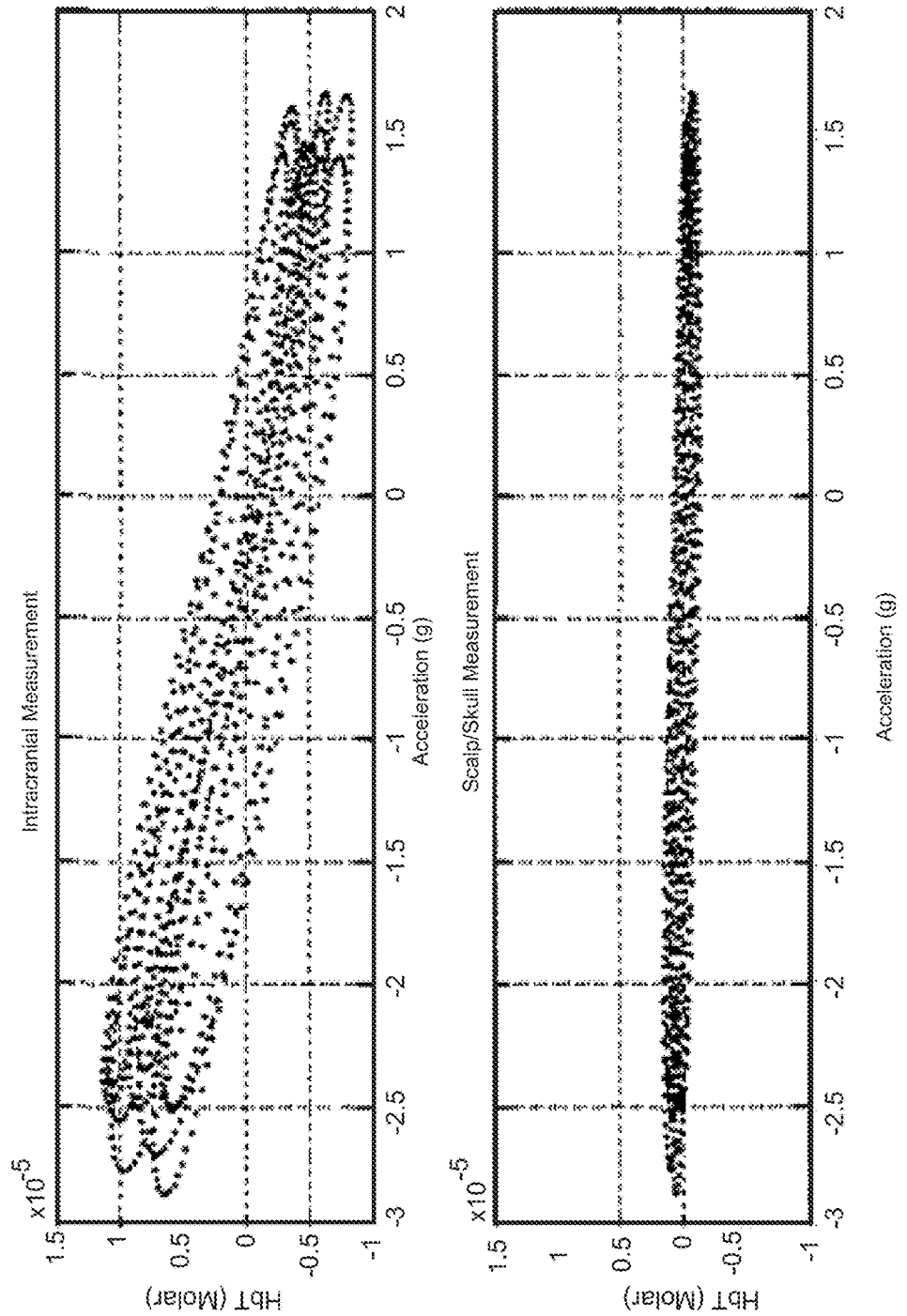
FIG. 8 is a graphic example illustrating the relationship between brain and scalp/skull signals versus accelerometry during head movement, in accordance with the present invention.

FIG. 8 shows a graphic example illustrating the relationship between brain and scalp/skull signals and accelerometry during head movement. A clear sensitivity can be seen to intracranial (brain) movement is visible in the top panel even for small accelerations of roughly 0.25 g, with no motion artifacts from the scalp and skull (bottom panel).

In summary, TBI is a major health problem and the most common cause of permanent disability in people under the age of 40, with nearly 180,000 sports-related TBI cases treated each year in emergency departments, and costs exceeding $100 billion. The present invention describes systems and methods that can use, for example, near-infrared spectroscopy (NIRS) of the head, or near-infrared neuromonitoring (NIN), to detect and quantify brain motion within an intact skull. Since approximately 80-90% of TBI is mild (mTBI), often exhibiting few symptoms or sequelae, the approach is sensitive to detecting brain movement even in the case of very mild head motions that generate no clinical sequelae.

The systems and methods described herein can combine mobile NIN technology with a physics model for photon propagation, as described above, and new techniques for enhancing NIN sensitivity to biological tissues, such as the brain. The systems and methods may be used to help validate computational models of brain motion, monitor the brain in models of head injury, quantify the brain motion associated with different types of acceleration/deceleration, and provide in-helmet monitoring during sporting events or on the sidelines, to name but a few applications. NIN also has the added advantage of being highly sensitive to cerebral blood volume and oxygenation, which are also important physiological variables for post-TBI brain assessment.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for assessing motion of a biological tissue of a subject, the biological tissue comprising one or more superficial biological layers and a targeted biological tissue, the system comprising:
one or more wearable elements configured to be arranged on the subject, the one or more wearable elements configured to allow transmission or reception of optical signals to and from the subject at one or more near-infrared wavelengths;
one or more perturbation units to provide an optical perturbation to the one or more superficial biological layers;
an optical signal generator configured to transmit optical signals at the one or more near- infrared wavelengths via the one or more wearable elements;
an optical signal receiver configured to acquire a set of optical signal data from the one or more wearable elements preceding, during, or following the optical perturbation at a first acquisition time relative to the optical perturbation; and
a signal processor configured to:
determine, using the set of optical signal data, a set of optical characteristics representative of light transiting the one or more superficial biological layers and the targeted biological tissue;
separate, using the set of optical characteristics and a model of the one or more superficial biological layers and the targeted biological layer, a target optical signal consistent with the targeted biological layer; and
generate a report indicative of a movement of the targeted biological tissue within the subject, wherein the movement of the targeted biological layer is calculated using the target optical signal.

2. The system of claim 1, wherein
the optical signal receiver is further configured to acquire a set of unperturbed optical signal data from the one or more wearable elements in the absence of the optical perturbation or preceding, during, or following the optical perturbation at a second acquisition time relative to the optical perturbation that is distinct from the first acquisition time.

3. The system of claim 2, wherein the signal processor is further configured to determine, using the set of optical signal data and the set of unperturbed optical signal data, the set of optical characteristics representative of light transiting the one or more superficial biological layers and the targeted biological tissue.

4. The system of claim 1, wherein the one or more near-infrared wavelengths are between about 650 nanometers and about 950 nanometers.

5. The system of claim 1, wherein the one or more perturbation units are configured to compress one or more blood vessels associated with the one or more superficial biological layers at a compression pressure that exceeds a pre-determined vascular pressure.

6. The system of claim 5, wherein
the pre-determined vascular pressure is between about 0.01 millimeters of mercury and about 1000 millimeters of mercury.

7. The system of claim 1, wherein the optical signal generator is further configured to acquire a set of unperturbed optical signal data from the wearable element in the absence of the optical perturbation or preceding, during, or following the optical perturbation at a second acquisition time relative to the optical perturbation that is distinct from the first acquisition time.

8. The system of claim 1, wherein the one or more superficial biological layers comprise a scalp tissue layer and a skull tissue layer.

9. The system of claim 1, wherein the targeted biological layer comprises a brain tissue layer.

10. The system of claim 1, wherein the one or more wearable elements comprise a first source-detector distance and a second source-detector distance that is different than the first source-detector distance.

11. The system of claim 10, wherein
the one or more wearable elements are configured to transmit and receive electromagnetic signals at a first near-infrared wavelength over the first source-detector distance and electromagnetic signals at the first near-infrared wavelength over the second source-detector distance.

12. The system of claim 11, wherein
the one or more wearable elements are configured to transmit and receive electromagnetic signals at a second near-infrared wavelength over the first source-detector distance and electromagnetic signals at the second near-infrared wavelength over the second source-detector distance, wherein the second near-infrared wavelength is different than the first near-infrared wavelength.

13. A system for assessing motion of a biological tissue of a subject, the biological tissue comprising one or more superficial biological layers and a targeted biological layer, the system comprising:
one or more wearable elements configured to be arranged on the subject, the one or more wearable elements configured to allow transmission or reception of optical signals to and from the subject at one or more near-infrared wavelengths;
one or more perturbation units to provide an optical perturbation to the one or more superficial biological layers;
an optical signal generator configured to transmit optical signals at the one or more near- infrared wavelengths via the one or more wearable elements;
an optical signal receiver configured to acquire a set of optical signal data from the one or more wearable elements preceding, during, or following the optical perturbation at a first acquisition time relative to the optical perturbation; and a signal processor configured to:
  determine, using the set of optical signal data, a set of optical characteristics and separate, using the set of optical characteristics, a target optical signal; and
  generate a report indicative of a movement of the targeted biological tissue within the subject, wherein the movement of the targeted biological layer is calculated using the target optical signal.

14. The system of claim 13, wherein the set of optical characteristics are representative of light transiting the one or more superficial biological layers and the targeted biological tissue.

15. The system of claim 13, wherein the signal processor is further configured to use a model of the one or more superficial biological layers and the targeted biological layer to separate the target optical signal.

16. The system of claim 13, wherein the target optical signal is consistent with the targeted biological layer.

17. The system of claim 13, wherein
  the optical signal receiver is further configured to acquire a set of unperturbed optical signal data from the one or more wearable elements in the absence of the optical perturbation or preceding, during, or following the optical perturbation at a second acquisition time relative to the optical perturbation that is distinct from the first acquisition time.

18. The system of claim 13, wherein the signal processor is further configured to determine, using the set of optical signal data and the set of unperturbed optical signal data, the set of optical characteristics representative of light transiting the one or more superficial biological layers and the targeted biological tissue.

19. The system of claim 13, wherein the one or more near-infrared wavelengths are between about 650 nanometers and about 950 nanometers.

20. A method for assessing motion of a biological tissue of a subject, the biological tissue comprising one or more superficial biological layers and a targeted biological layer, the method comprising:
  providing one or more wearable elements configured to be arranged on the subject, the one or more wearable elements configured to allow transmission or reception of optical signals to and from the subject at one or more near-infrared wavelengths;
  providing an optical perturbation to the one or more superficial biological layers;
  transmitting optical signals at the one or more near-infrared wavelengths via the one or more wearable elements;
  acquiring a set of optical signal data from the one or more wearable elements preceding, during, or following the optical perturbation at a first acquisition time relative to the optical perturbation; determining, using the set of optical signal data, a set of optical characteristics representative of light transiting the one or more superficial biological layers and the targeted biological tissue;
  separating, using the set of optical characteristics and a model of the one or more superficial biological layers and the targeted biological layer, a target optical signal consistent with the targeted biological layer; and
  generating a report indicative of a movement of the targeted biological tissue within the subject, wherein the movement of the targeted biological layer is calculated using the target optical signal.

* * * * *